(12) United States Patent
Butterfield et al.

(10) Patent No.: US 9,302,091 B2
(45) Date of Patent: Apr. 5, 2016

(54) CHECK VALVE SYSTEM

(71) Applicant: CareFusion 303, Inc., San Diego, CA (US)

(72) Inventors: Robert Dwaine Butterfield, San Diego, CA (US); Andre Gamelin, San Diego, CA (US); Neil Quitoviera, San Diego, CA (US); Daniel Abal, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 447 days.

(21) Appl. No.: 13/940,917

(22) Filed: Jul. 12, 2013

(65) Prior Publication Data

US 2015/0018780 A1   Jan. 15, 2015

(51) Int. Cl.
*A61M 5/00* (2006.01)
*A61M 39/22* (2006.01)
*A61M 39/24* (2006.01)

(52) U.S. Cl.
CPC ......... *A61M 39/22* (2013.01); *A61M 2039/224* (2013.01); *A61M 2039/244* (2013.01)

(58) Field of Classification Search
CPC ................. A61M 2039/224; A61M 2039/244; A61M 39/22
USPC ........................................................ 604/246
See application file for complete search history.

(56) References Cited

U.S. PATENT DOCUMENTS

| | | | | |
|---|---|---|---|---|
| 4,084,606 A | * | 4/1978 | Mittleman | A61M 5/00 137/102 |
| 5,556,386 A | * | 9/1996 | Todd | A61M 1/3664 137/510 |
| 2011/0282276 A1 | * | 11/2011 | Abal | A61M 5/14212 604/33 |
| 2011/0319836 A1 | * | 12/2011 | Lee | A61M 5/16813 604/248 |

* cited by examiner

*Primary Examiner* — Jason Flick
(74) *Attorney, Agent, or Firm* — Fred C. Hernandez; Mintz Levin Cohn Ferris Glovsky and Popeo, P.C.

(57) ABSTRACT

A pressure-maintaining valve assembly can be coupled to the tubing of an infusion pump system. The valve assembly includes an element that regulates fluid flow through the tubing. This element may also act as a one way or check valve.

20 Claims, 11 Drawing Sheets

CHECK VALVE SYSTEM

BACKGROUND

An infusion system for delivering a drug or other liquid into a patient typically includes a pump segment that couples to an infusion pump. The pump segment typically includes a tube segment that is operated upon by a pump mechanism for pumping fluid from a source of fluid, such as an intravenous (IV) bag toward the patient.

The tube segment may be made of a material, such as silicone, that is sufficiently pliable to be acted upon by the pump mechanism in order to create a repeatable volumetric displacement in the tube segment for causing fluid flow. Such a pliable material may also be at least partially permeable, which under some conditions, permits air to enter the tube segment, which is generally undesirable. In addition, dissolved air in the IV fluid and air introduced into the tube during priming may also be present. There is a need for devices and methods for dealing with air-in-line conditions for infusion pump systems.

SUMMARY

In one aspect, there is disclosed one aspect, a pump cassette for coupling with a pump device, the pump cassette comprising: a pliable fluid pumping segment adapted for passage and propulsion of an infusion fluid toward a patient; a valve assembly coupled to the pumping segment for controlling fluid flow through and pressure within the pumping segment, wherein the valve assembly has the following states: (a) a flow state wherein the valve assembly permits restricted flow through the fluid lumen; (b) a constant-pressure state wherein the valve assembly permits flow through the fluid lumen at a predetermined sustaining pressure independent of flow rate; and (c) a non-flow state wherein the valve assembly completely blocks flow through the fluid lumen.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

Like reference symbols in the various drawings indicate like elements.

DETAILED DESCRIPTION

Disclosed is a pressure-maintaining valve assembly that can be coupled to the tubing of an infusion pump system. The valve assembly includes an element that regulates fluid flow through the tubing. This element may also act as a one way or check valve. The check valve causes the fluid entering it to sustain a nominal pressure at any flow rate, which can be used to drive air that may be present such as due to 'outgassing' out of the tubing such as through the permeable material of the tubing. The valve pressure can also be used to prevent air from entering the tubing via the permeable material of the tubing. A positive internal pressure of as little as 7-10 inches water has been shown to be sufficient to eliminate air ingress. The valve assembly may be used as an integral part of a pump segment portion of the infusion system or it can be a separate component that is located downstream of the pump segment. When a check valve type assembly is properly in place, it has the additional benefit of preventing unintended back flow of fluid and fluid pressure into the pliable tubing due to common practices of introducing manual fluid injections downstream from the pump. If the valve is designed to sustain pressure (sometimes called 'sustaining' pressure) greater than the potential gravity elevation pressure that might be provided when the IV set is not installed in the pump, then another benefit arises from prevention of inadvertent uncontrolled gravity free flow.

Figure 1:
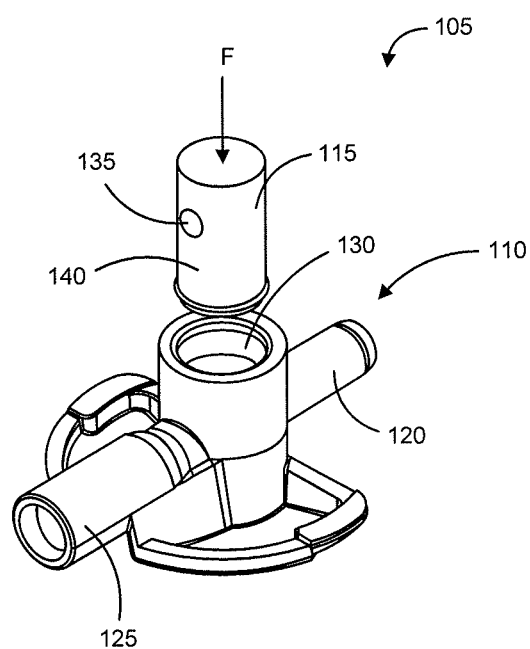
FIG. 1 shows a perspective, exploded view of an exemplary embodiment of a valve assembly.

FIG. 1 shows a perspective, exploded view of an exemplary embodiment of a valve assembly 105, which includes a valve body 110 and an actuator 115 movably coupled to the valve body 110. As mentioned, the valve assembly 105 can be used as part of an infusion pump system and integrally incorporated into a pump segment of the infusion pump system. Or the valve assembly 105 may be a stand-alone component that is added to an infusion pump system, such as in an adjunct or add-one scenario.

The valve body 110 includes an inlet port 120 with an internal lumen through which fluid may flow into the valve body 110. The valve body 110 also includes an outlet port 125 with an internal lumen through which fluid may flow out of the valve body 110. The inlet port 120 and the outlet port 125 may both be connected to respective tubing through which fluid may flow into and out of the valve body 110.

With reference still to FIG. 1, the valve body includes a vertical passageway 130 sized and shaped to slidably receive the actuator 115. The actuator 115 is shown in the form of a cylindrical plug or piston although the actuator may vary in size and shape from what is illustrated. The actuator 115 includes a passageway 135 that aligns with the inlet port 120 and outlet port 125 when the actuator 115 is properly positioned within the opening 130, as described more fully below. The actuator also includes a pressure valve 140 that is configured to sustain a constant pressure independent of flow rate. The pressure valve 140 may also be aligned with the inlet port 120 and outlet port 125 when the actuator 115 is properly positioned within the opening 130, as described more fully below. It should be appreciated that the type of valve may vary and is not limited to a specific valve type. The valve 140 may be a slit valve that is configured to open at a predetermined cracking pressure.

In an embodiment, the actuator 115 is actuated by applying a force F that can move the actuator 115 upward and/or downward through the passageway 130. The actuator 115 may be spring loaded or otherwise biased toward a particular state. Or the actuator may be configured to remain in a particular state once set there.

An operator actuates the actuator 115 to achieve different flow states for the valve assembly 105. Or, the pump device itself can automatically actuate the actuator. In a first, or standard state, the actuator 115 may be actuated to a position that achieves regulated flow through the valve assembly, wherein flow from the inlet port 120 to the outlet port 125 is permitted only when a predetermined sustaining pressure is achieved within the valve assembly 105. The actuator may also be moved to a priming state that achieves free-flow through the valve assembly from the inlet port 120 to the outlet port 125, as described more fully below.

This is described in more detail with reference to FIG. 2, which shows the valve assembly 105 in an assembled state with the actuator 115 positioned in the standard, or back-pressure, state for standard operation. The valve assembly 105 may be positioned in the standard pressure state, for example, by exerting a downward force F onto the actuator 115 such that the pressure valve 140 moves to align with the inlet port 120 and outlet port 125. The actuator 115 may include one or more detents 205 that releasably interlock with the valve body 110 to releasably maintain the actuator 115 in the standard state.

Figure 2:
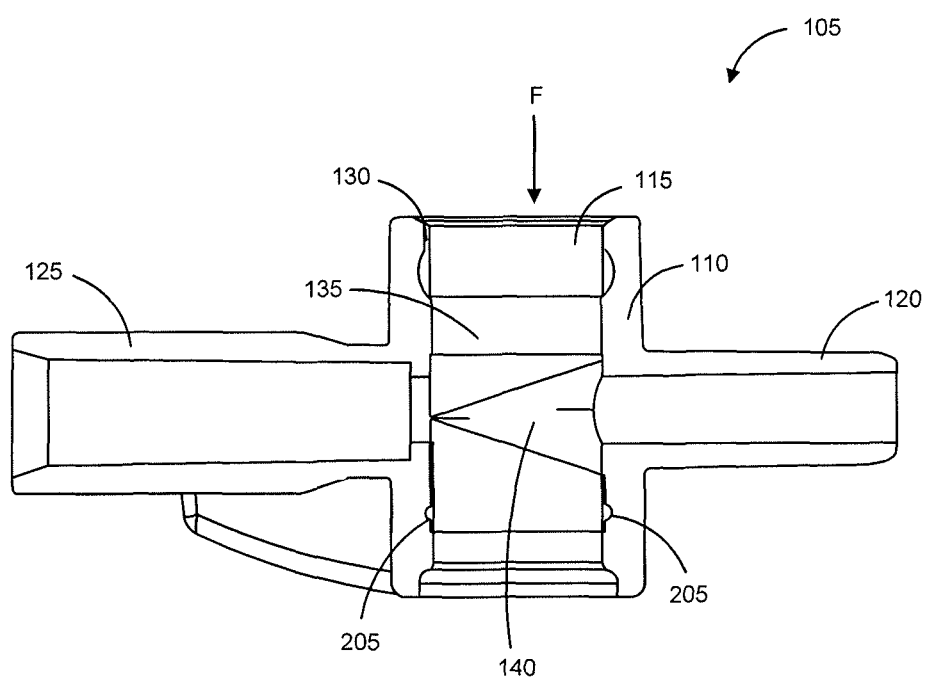
FIG. 2 shows the valve assembly of FIG. 1 in standard, regulated flow state.

With reference still to FIG. 2, when the valve assembly 105 is in the standard state, the actuator 115 is positioned within the vertical passageway 130 such that the pressure valve 140 aligns with the inlet port 120 and the outlet port 125. In this manner, the pressure valve 140 must open in order for fluid to flow from the inlet port 120 to the outlet port 125. As mentioned, the pressure valve 140 is configured to open at a predetermined sustaining pressure. In an embodiment, the sustaining pressure of the valve 140 is about 4 pounds per square inch (psi) although the selected sustaining pressure may vary. A 4 psi sustaining pressure (104 inches of water column) may be advantageous as it is higher than the typical maximum head pressure that is caused by an IV bag (72 inches of water column) in an infusion pump system and so can be used to prevent unintentional gravity flow through the tubing since when the hydrostatic pressure applied to the valve is less than the sustaining pressure, there can be no flow through the valve. In another embodiment, the sustaining pressure is in the range of about 2-6 psi.

It should be appreciated that the pressure valve 140 is exemplary and that other types of valve configurations may be used. The pressure valve is advantageous in that it provides a low profile. In addition, the actuator 115 may take on different shapes and may be actuated in manners other than linear movement. For example, the actuator may be configured to be actuated through rotation. The actuator can also be actuated by the pump device.

Figure 3:
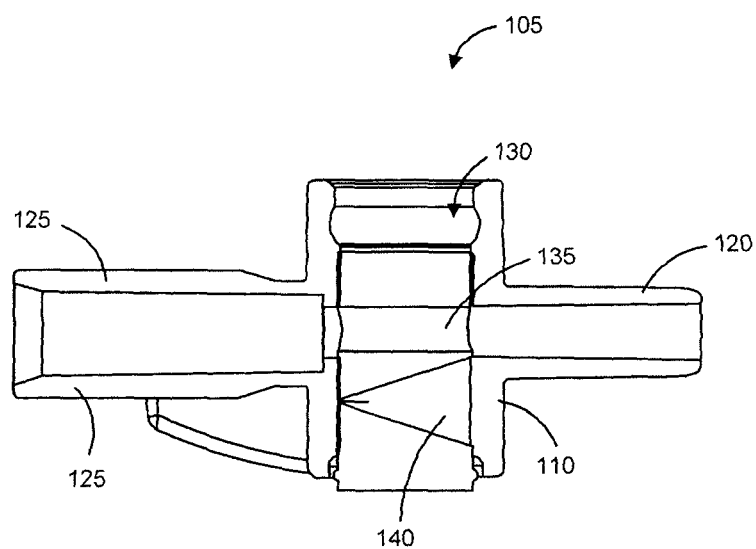
FIG. 3 shows the valve assembly of FIG. 1 a priming state.

FIG. 3 shows the valve assembly 105 after the actuator 115 has been actuated to cause the valve assembly to be in a priming state. When the valve assembly 105 is in the priming state, the actuator 115 is positioned within the vertical passageway 130 such that the passageway 135 is aligned with the inlet port 120 and the outlet port 125. Thus, there is no blockage or regulator of fluid flow between the inlet port 120 and the outlet port 125. Fluid may therefore flow freely from the inlet port 120 to the outlet port 125 when the valve assembly 105 is in the priming state.

FIG. 3 shows the priming state as having completely maximum flow potential unrestricted through the valve assembly. In an alternate embodiment, the priming state has a resistance to flow through the valve assembly that permits some flow at a limited flow rate. This may be desirable during priming of the tubing as fluid flow at too high of a fluid flow rate may result in introduction of air into the tubing. The nurse may employ adjustment of the available elevation differential (aka 'head') and or the adjustment of a separate roller-clamp variable flow restrictor when using the priming state.

Figure 4:
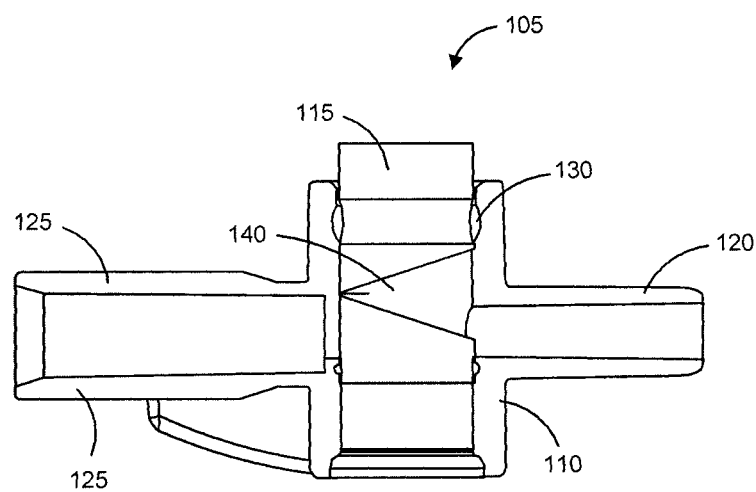
FIG. 4 shows the valve assembly in a no flow state.

The valve assembly 105 may also be in a no-flow state wherein fluid flow from the inlet port 120 to the outlet port 125 is inhibited or completely blocked. FIG. 4 shows the valve assembly in a no flow state. When the valve assembly 105 is in the no flow state, the actuator 115 is positioned within the vertical passageway 130 such that at least a portion of the actuator 115 blocks flow from the inlet port 120 to the outlet port 125. As mentioned, the actuator 115 can be moved to various positions within the passageway 130 by exerting an upward or downward force F upon the actuator. Whether an upward or downward force is exerted depends on the current position of the actuator 115 and the valve state that is sought to be achieved.

In use, the valve assembly 105 is coupled to the tubing or tube of an infusion system configured for pumping fluid to a patient, such as the system schematically shown and described below with reference to FIG. 5. The valve assembly 105 may be incorporated directly into a pump cassette (sometimes referred to as a pump segment) of the infusion system or the valve assembly may be incorporated into any portion of the tube downstream of the pump cassette.

The valve assembly 105 blocks fluid from passing through the tubing until the sustaining pressure of the valve assembly is exceeded. This results in a flow-independent pressure existing in the intake side of the tubing. As mentioned, the valve assembly 105 when in the standard (constant pressure) state (shown in FIG. 2) creates an intake (to the valve) pressure that must be overcome for fluid to flow through the valve assembly 105. This back "intake" pressure is applied to the pumping tubing and can be used to expel air in attached tubing out through the permeable material of this tubing. The constant valve pressure also prevents are from entering the tubing via the permeable material. The tubing may be made, for example, of silicone rubber.

A user may initially set the valve assembly 105 to the priming state in order to prime the tubing prior to pumping. The user may then actuate the valve assembly to set it to the free flow state or the standard state.

Figure 5:
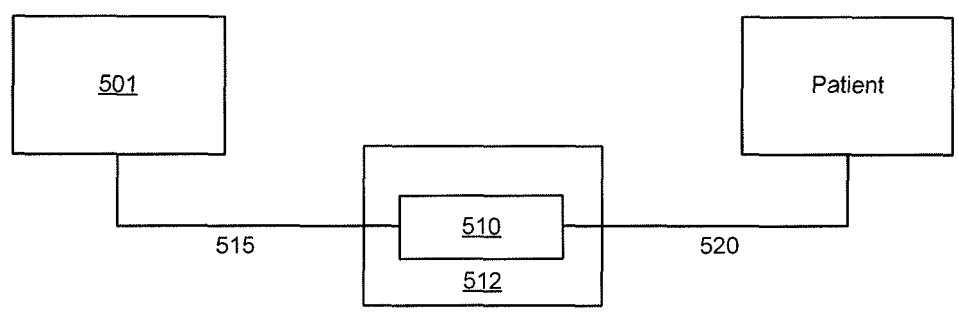
FIG. 5 shows a schematic view of an infusion system configured for pumping a fluid to a patient.

FIG. 5 shows a schematic representation of an infusion system 500 configured to be used in pumping a fluid to a patient. The infusion system 500 includes a fluid container, such as an intravenous (IV) bag 501, fluidly coupled to a pump cassette 510 via a fluid conduit, such as a tube 515. The pump cassette 510 is configured for pumping fluid from the IV bag 501 toward a patient via a tube 520 when the pump cassette 510 is coupled to a modular pump device. The pump cassette 510 is configured to be removably coupled to the modular pump device 512 such as by inserting the pump cassette 510 into a seat of the modular pump device 512. The modular pump device 512 may include a mechanism that is configured to automatically set the valve assembly 105 to one of the standard (pressure), priming (restriction), or unrestricted flow states when the pump segment 510 is inserted into the modular pump device 512. The pump device may also actuate the state of the valve automatically to one or more of the specified states.

With reference still to FIG. 5, the tube 515 has a proximal end fluidly coupled to (such as via a drip chamber) the IV bag 501, and a distal end fluidly coupled to a pumping segment 505 of the pump cassette 510. Likewise, the tube 520 has a proximal end fluidly coupled to a fluid lumen of the pump segment 510 and a distal end that attaches to the patient via an IV connection. Either of the tubes 515 or 520 may be formed of a single tube or may be formed of a series of tubes removably attached to one another, such as in an end-to-end manner using any of a variety of connectors such as Luer connectors. The tubes 515 and 520 and the pumping segment 505 (FIG. 6) of the pump cassette 510 collectively form a continuous fluid lumen that provides a fluid pathway from the IV bag 501 toward the patient. The combinations of components 515 (with drip chamber), 510 and 520 (with Luer fitting) comprise what is termed an "IV set". This continuous fluid lumen may include any of a variety of components that facilitate or otherwise are used in connecting the tubes and/or pumping fluid, including, for example, valves, filters, free-flow stop valves, pressure and air detection regions or components and access connectors, etc. Any of a variety of additional components may be used, including, for example, anti-free flow devices, pressure sensing components, air detection components, etc.

Figure 6:
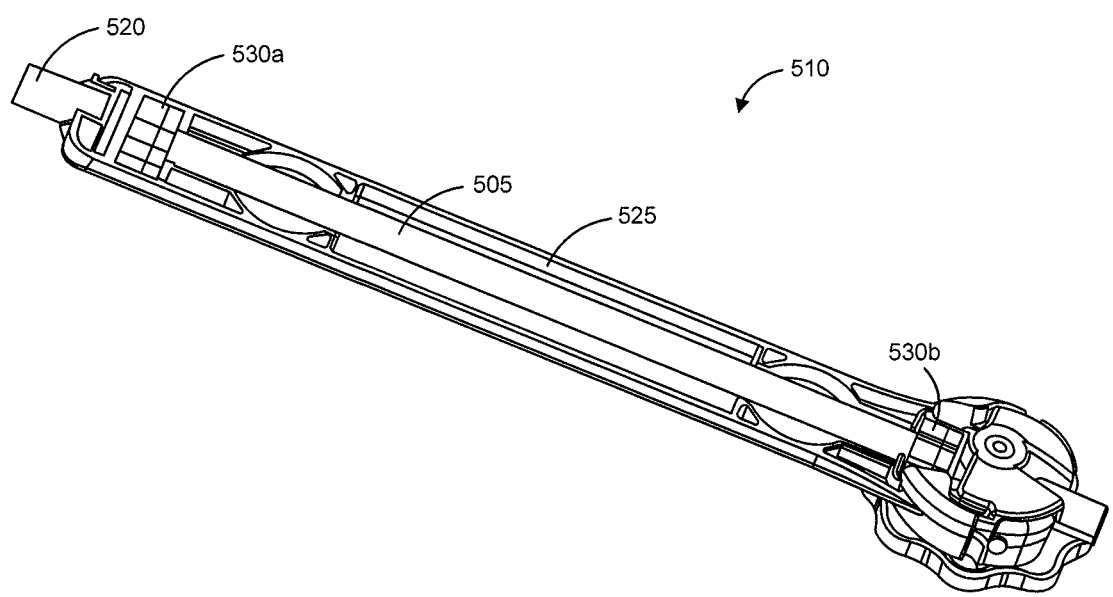
FIGS. 6 and 7 shows perspective views of an exemplary pump segment.
Figure 7:
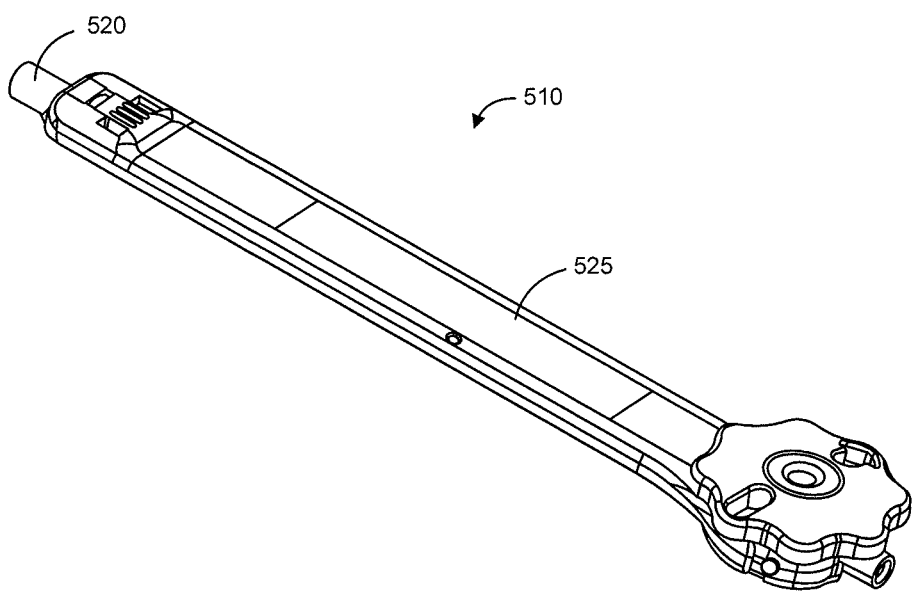

FIGS. 6 and 7 shows perspective views of an exemplary pump cassette 510. The valve assembly 105 may be incorporated into the pump segment 510 such that it regulates fluid flow through the pump segment.

As mentioned, the pump cassette 510 may be in the form of an assembly that removably inserts into a modular pump device. With reference to FIG. 6, the pump cassette 510 includes the pumping segment 505 formed of tubing having an internal fluid lumen. When the cassette 510 is attached to the tubes 115 and 120, the fluid pumping segment 505 fluidly connects the tube 515 to the tube 520. The fluid pumping segment 505 may be acted upon by any of a variety of pump mechanisms of the modular pump device to pump fluid through the pumping segment 505 in order to achieve fluid flow from the IV Bag 501 to or toward the patient.

A proximal end of the pumping segment structure is fluidly and mechanically attached to the tube 115, such as via a connector 520. A distal end of the pumping segment structure is attached to the tube 120, such as via a valve assembly 105. The pumping segment 505 may also be formed of two or more structures that collectively define the pumping segment 505 therebetween.

The pump cassette 510 may have an integrated air collection chamber or an "air trap" system that is configured to collect air. The air collection chamber permits air introduced from other means to be kept from traveling through the air sensor and towards the patient. The integrated air collection chamber may be collapsible to allow proper priming of the set.

With reference still to FIGS. 6 and 7, the pumping segment 505 is positioned on a frame 525. The frame 525 is formed of a relatively hard or rigid material such that the frame may act as a platen relative to the fluid lumen of the pumping segment 505 for pumping fluid through the fluid lumen.

The relatively rigid structure of the frame 525 can be used to secure the pumping segment 505 in a fixed position and/or shape relative to the frame 525, such as to eliminate or reduce the risk of the pumping segment 505 being unintentionally stretched or moved during positioning of the frame 525 into the modular pump device. Moreover, the rigid structure of the frame 525 may be used to provide a controlled degree of stretching of the pumping segment 505 to enhance the accuracy of the achieved fluid flow rate. It should be appreciated that accidental or unintended stretching or deformation of the pumping segment 505 may interfere with pumping accuracy as such stretching or deformation will change the flow geometry. The rigid frame 525 and the clips 530 that secure the pumping segment 505 to the frame 525 can be used to secure the fluid lumen 505 in a predetermined, fixed geometry that is unlikely to incur undesired deformation or stretching.

One or more attachment members, such as clips 530, are configured to secure the pumping segment 505 to the frame 525. In the illustrated version, two clips 530a and 530b are positioned over the pumping segment 505 and attached to the frame 525 such that the clips 530 secure the pumping segment 505 to the frame 525. The first clip 530a is located near one end of the pumping segment 505 and the second clip 530b is located near an opposite end of the pumping segment 505. It should be appreciated, however, that various quantities of clips may be used at any of a variety of locations along the pumping segment 505 and/or the frame 525.

Figure 8:
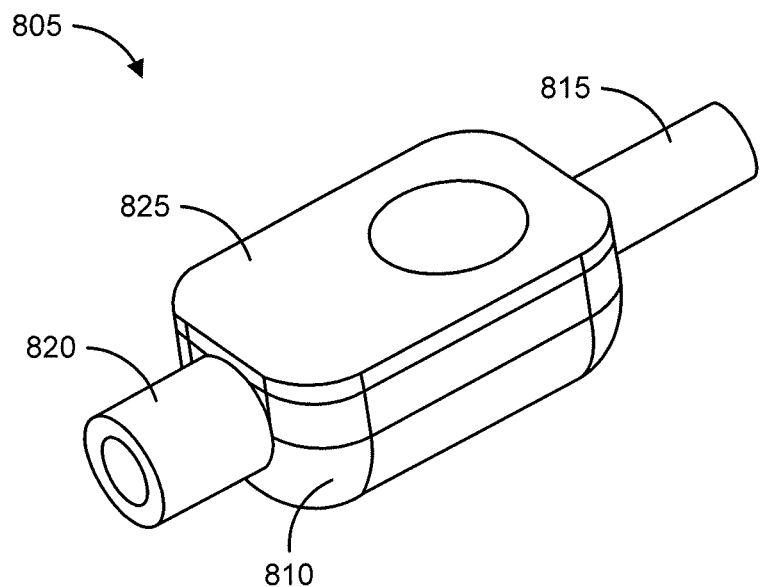
FIGS. 8-11 show another embodiment of a valve assembly.

FIG. 8 shows a perspective view of another embodiment of a valve assembly 805. The valve assembly has an outer housing 810 coupled to a fluid inlet 815 and a fluid outlet 820. A cover in the form of a membrane 825 is positioned on the housing 810 so as to cover an internal cavity. The membrane 825 can be actuated to control a valve member inside the housing 810 and thereby control fluid flow through the housing 810 from the fluid inlet 815 toward the fluid outlet 820.

Figure 9:
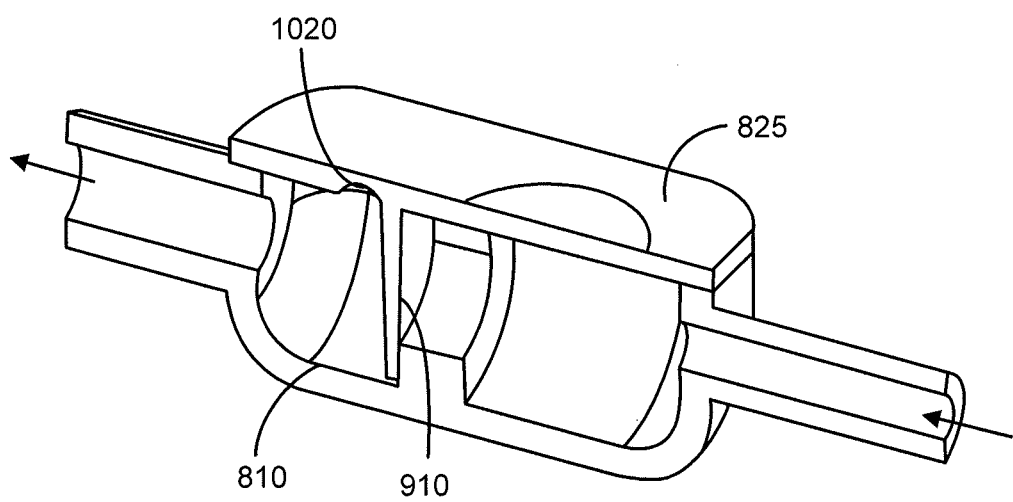

With reference to the cross-sectional view of FIG. 9, the housing defines an internal chamber through which fluid may flow from the inlet 815 toward the outlet 820. As mentioned, a valve member 910 is positioned inside the housing 810. The valve member 910 regulates fluid flow from the inlet 815 toward the outlet 820, as described more fully below. In an embodiment, the valve member 910 is a flap that extends downwardly from the membrane 825 toward a seal lip 915. In a default state shown in FIG. 9, the valve member 910 sealingly engages the seal lip 915 to block flow and prevent fluid from flowing across the valve member 910 from the inlet 815 to the outlet 820. The valve member 910 is coupled to the membrane 825 such that predetermined movement or deformation of the membrane 825 results in displacement of the valve member 910 away from seal lip 915 so as to form an opening through which fluid may flow. Thus, when the valve member 910 disengages from the seal lip 915, fluid is permitted to flow across the valve member 910 from the inlet 815 toward the outlet 820. This is described in more detail with reference to FIGS. 10 and 11, which show additional views of the valve assembly 805.

Figure 10:
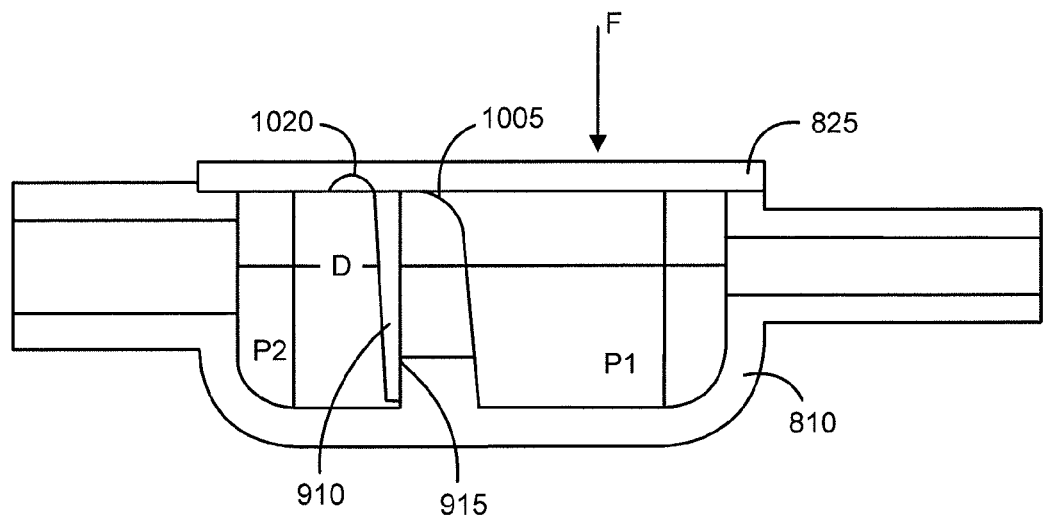
Figure 11:
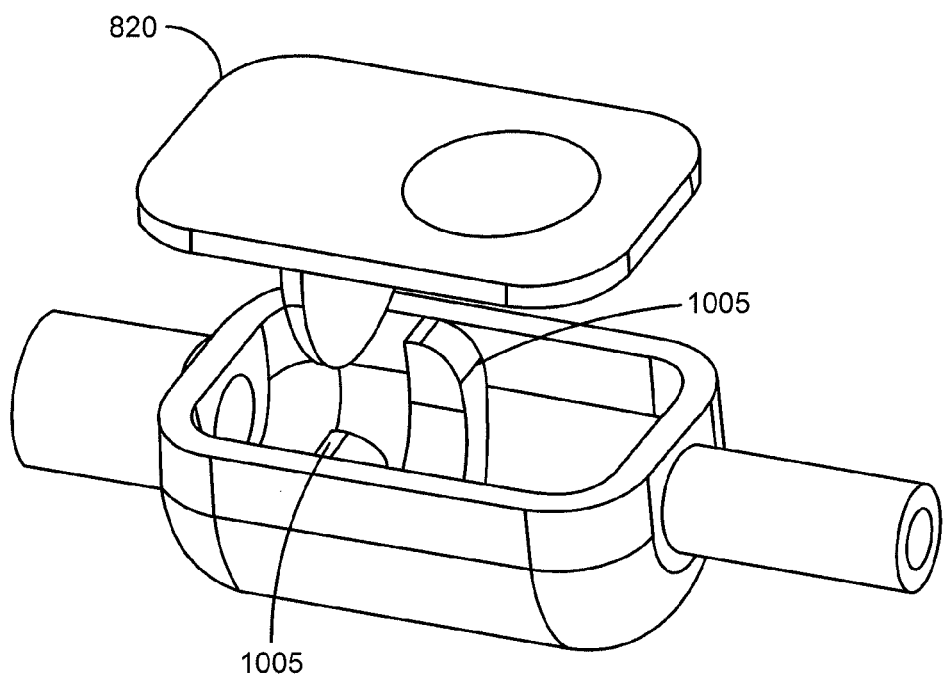

With reference to FIGS. 10 and 11, one or more fulcrum structures 1005 are positioned inside the housing 810. The structures 1005 are sized, shaped, and positioned to engage a bottom surface of the membrane 825 such that the fulcrum structures 1005 may serve as one or more fulcrums relative to the membrane 825. That is, when a downward force F (FIG. 10) is applied to the membrane 825, the membrane 825 engages the fulcrum structure 1005 and pivots about a location 1020 such that the valve member moves in a direction D away from the seal lip 915. In this manner, the valve member 910 disengages from the seal lip 915. An opening is thus formed for fluid to flow past the valve member 910.

The downward force F may be applied manually to open the valve member 910 and provide fluid flow, such as by a user pressing downward on the valve member 910. The valve member 910 may also open as a result of fluid pressure P1 (FIG. 10) exceeding fluid pressure P2 inside the housing, which will then force the valve member in the direction D to open the valve member.

Figure 12:
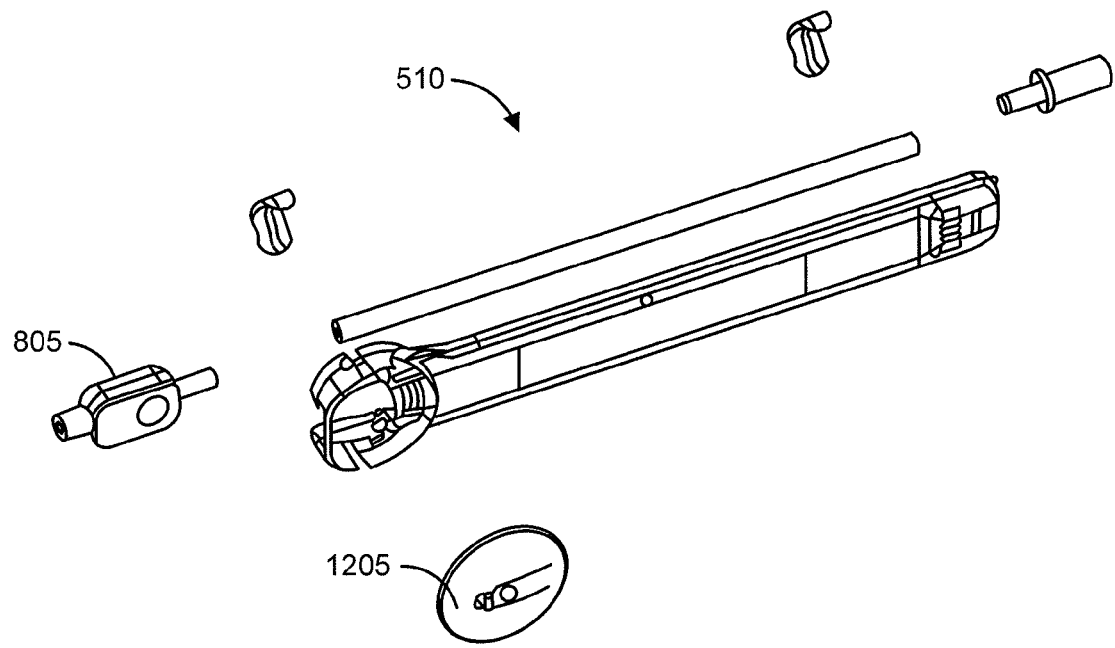
FIGS. 12-13 show the valve assembly of FIGS. 8-11 as part of an infusion cassette.
Figure 13:
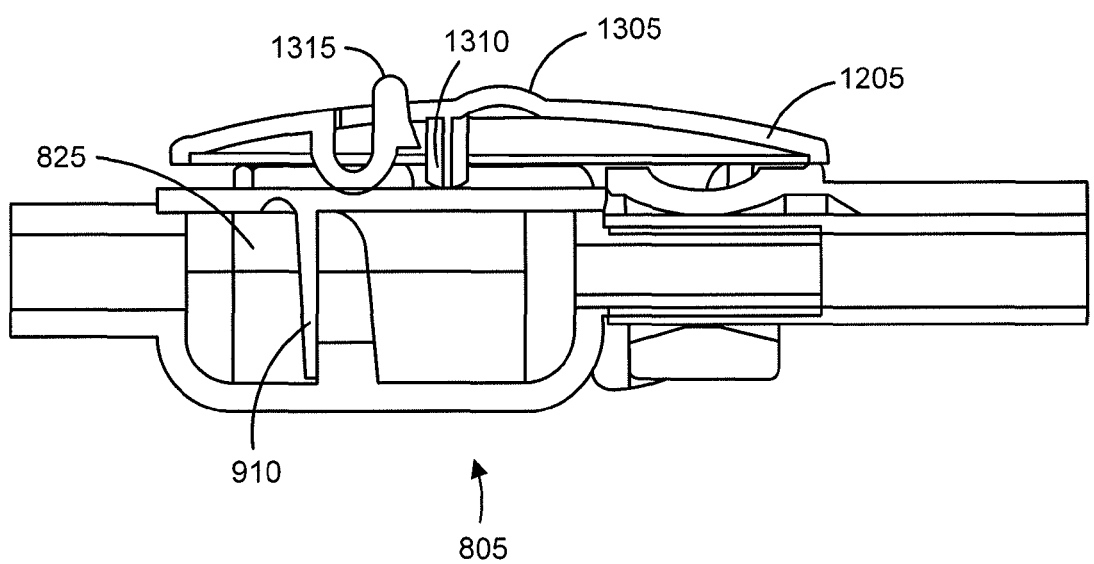

With reference now to FIG. 12, the valve assembly 805 may be coupled to a pump cassette 510 such as the pump cassette described above with reference to FIGS. 6 and 7. FIG. 12 shows the pump cassette 510 in an exploded state. A cover 1205 is configured to be removably positioned atop the valve assembly 805. FIG. 13 shows a cross-sectional view of the valve assembly 805 coupled to the assembled cassette 510. As mentioned, the cover 1205 is positioned atop the valve assembly 805. The cover 1205 provides a push button 1305 that can be manually pressed downward toward the valve assembly 805. The push button 1305 is connected to a push arm 1310 that contacts the membrane cover 825 of the valve assembly. When the push button 1305 is pressed downward toward the membrane cover 825, the push arm 1310 exerts a force onto the membrane cover 825, which force opens the valve member 910 in the manner described above with reference to FIG. 10. Any of a variety of mechanisms, such as a clip 1315, may be used to removably secure the cover 1205 to the valve assembly.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

The invention claimed is:

1. A valve system for coupling with a pump device, the valve system comprising:
   a pliable fluid pumping segment adapted for passage and propulsion of an infusion fluid toward a patient; and
   a valve assembly coupled to the pumping segment for controlling fluid flow through and pressure within the pumping segment, wherein the valve assembly has the following states:
   (a) a flow state wherein the valve assembly permits restricted flow through the pumping segment;
   (b) a constant-pressure state wherein the valve assembly permits flow through the pumping segment at a predetermined sustaining pressure independent of flow rate; and
   (c) a no-flow state wherein the valve assembly completely blocks flow through the pumping segment.

2. A valve system as in claim 1, wherein the valve assembly permits fluid flow through the pump segment while maintaining independent of flow rate a predetermined pressure within the pump segment.

3. A valve system as in claim 2, wherein the valve assembly comprises a constant pressure valve.

4. A valve system as in claim 1, wherein the constant pressure which is independent of flow rate is in the range of 2-6 psi.

5. A valve system as in claim 1, wherein the valve assembly provides some resistance to fluid flow through the pumping segment when the valve assembly is in the flow state.

6. A valve system as in claim 1, wherein the valve assembly minimally restricts through the pumping segment when the valve assembly is in the flow state.

7. A valve system as in claim 1, wherein the pumping segment is manufactured of silicone rubber.

8. A valve system as in claim 1, wherein the valve assembly includes an actuator that can be actuated to set the state of the valve assembly.

9. A valve system as in claim 8, wherein the actuator may be manually actuated.

10. A valve system as in claim 8, wherein the valve assembly may be actuated upon insertion into a pump.

11. A valve system as in claim 8, wherein the valve assembly may be automatically actuated by a pump.

12. A valve system as in claim 8, wherein the actuator is actuated via sliding or rotational movement.

13. A valve system as in claim 1, wherein the valve assembly comprises a valve body having an inner lumen, an inlet to the lumen, and an outlet from the lumen, the valve assembly further comprising a cylindrical piston movably positioned in the valve body, wherein the position of the piston in the valve body controls the state of the valve assembly.

14. A valve system as in claim 13, wherein the valve body has a passageway that aligns with the inlet and outlet when in the flow state.

15. A valve system as in claim 13, wherein the piston in the valve body has a pressure regulating element that aligns with the inlet and outlet when in the constant-pressure state.

16. A valve system as in claim 13, wherein the piston in the valve body blocks flow from the inlet to the outlet when in the no-flow state.

17. A valve system as in claim 13, further comprising a frame coupled to the fluid lumen and the valve assembly, the frame adapted to be inserted into a seat of a pump device.

18. A valve system as in claim 13, wherein the valve assembly further has:
   a no-flow state wherein the valve assembly completely blocks flow through the fluid lumen.

19. A valve system as in claim 1, further comprising an air collection chamber.

20. A valve system as in claim 1, wherein the valve assembly comprises a flap valve.

* * * * *